United States Patent [19]

Giese

[11] Patent Number: 4,709,016

[45] Date of Patent: Nov. 24, 1987

[54] MOLECULAR ANALYTICAL RELEASE TAGS AND THEIR USE IN CHEMICAL ANALYSIS

[75] Inventor: Roger W. Giese, Quincy, Mass.

[73] Assignee: Northeastern University, Boston, Mass.

[21] Appl. No.: 344,394

[22] Filed: Feb. 1, 1982

[51] Int. Cl.[4] .................. C07H 15/12; C07D 213/28; G01N 53/00

[52] U.S. Cl. .................................. 530/389; 530/390; 530/391; 260/543 R; 548/342; 536/27; 435/7; 436/547; 436/536; 436/2; 562/553; 562/559; 562/579

[58] Field of Search .................... 260/112.5, 543 R; 424/177, 94, 1, 12; 436/2, 536, 501, 547; 435/7, 188, 12, 424, 260, 175, 181, 183; 548/542; 530/389, 390, 391; 536/27

[56] References Cited

U.S. PATENT DOCUMENTS

| | | | |
|---|---|---|---|
| 4,182,656 | 1/1980 | Ahnell et al. | 435/34 |
| 4,231,999 | 11/1980 | Carlsson et al. | 424/1 |
| 4,331,590 | 5/1982 | Bocuslaski et al. | 260/112 B |
| 4,360,592 | 11/1982 | Weltman | 435/7 |
| 4,423,143 | 12/1983 | Rubenstein et al. | 435/7 |

OTHER PUBLICATIONS

Carlsson et al., *Biochem J. vol. 173*, pp. 723-737—1978, "Protein Thiolaticin and Reversible Protein-Protein Conjugation".

Poole et al., *Analytical Chemisty*, vol. 52, No. 9, Aug. 1980.

Gross, Erhard, *Methods in Enzymology*, II, pp. 238-253.

Jacobs et al., *Journal Biological Chemistry*, vol. 250, pp. 3629-3636.

Giese, R. W. et al., *C&EN*, "Release Tags, A New Class of Analytical Reagents", Feb. 15, 1982 (including R. Joppich-Kuhn).

Giese, R. W. et al., (including R. Joppich-Kuhn), Program and Abstracts for the 14th Annual Symp. on Adv. Anal. Concepts", Apr. 29, 1982.

Giese, R. W. et al., (including R. Joppich and J. A. Corkill), FACSS Final Program, Special Events, Abstracts of 9th Ann. Meeting, Sep. 29, 1982.

Joppich-Kuhn, Regula et al.; *Clinical Chemistry*, vol. 28, No. 9, "Releax Tags: A New Class of Analytical Reagents", 5/16/1982.

*Primary Examiner*—Thomas G. Wiseman
*Assistant Examiner*—Robin Lyn Teskin
*Attorney, Agent, or Firm*—Weingarten, Schurgin, Gagnebin & Hayes

[57] ABSTRACT

A new class of chemical reagents called release tags which comprise signal, release and reactivity groups is disclosed and a release tag involving a pentafluorobenzoyl signal group, a methionylamide release group, and an active ester reactivity group is used to analyze the hormone, thyroxine, in serum, involving quantitation of the released signal group by gas chromatography with electron capture detection.

10 Claims, No Drawings

MOLECULAR ANALYTICAL RELEASE TAGS AND THEIR USE IN CHEMICAL ANALYSIS

FIELD OF THE INVENTION

This invention relates to chemical analysis, both qualitative and quantitative, and, more particularly, to a new class of reagents serving as molecular labels or tags in analytical procedures.

BACKGROUND OF THE INVENTION

Sensitive and specific chemical labels or signal groups are widely used in chemical analysis. These labels include radioactive atoms, fluorescent reagents, luminescent molecules, metal-containing compounds, electron absorbing substances, and light absorbing compounds. In each case, one or more techniques are available to measure the particular label of interest. For example, in the case of electron-absorbing labels, measurements can be carried out by gas chromatography with electron capture detection (GC-ECD).

Not all analytical procedures involve the use of such chemical labels, but generally those applicable procedures can be divided into three broad categories. In the first category, the substance to be measured (analyte substance or analyte) is reacted with the label during the analytical procedure, leading to a labeled analyte. The signal from this labeled analyte then provides a measurement of the analyte substance. In the second category, the analyte in the sample is not labeled, but a labeled internal standard, labeled comparison substance, or labeled specifc binding partner is employed in the procedure. An example of the second category is the use of chemical tracers in radioimmunoassay or immunoradiometric assay procedures. The third analytical category is exemplified by the double isotope derivative technique. This technique involves both labeling of the analyte and the use of one or more labeled internal standards. The labeled internal standard substances may be labeled additionally in this isotope derivative procedure along with the analyte.

There are major shortcomings associated with each of the types of chemical labels currently employed in analytical procedures. For example, the use of radiolabels, particularly the more sensitive radiolabels like $^{125}I$, is limited by their short half-lives; by the physical instability and tendency for chemical lability with these labels; by safety and disposal considerations; and by the unavailability of several, closely related forms which can be measured simultaneously with comparable sensitivity and complete discrimination. Radiolabels like $^3H$ or $^{14}C$ are limited in these same respects (except for the longer half-lives of $^3H$ and $^{14}C$), and are limited additionally by their lower sensitivity and by the susceptibility of the beta signals from these labels to quenching in the sample or liquid scintillation matrix used for counting of the label.

Many of these same limitations also apply to the use of other types of labels, particularly the problem that the magnitude of the signal from these nonradioactive labels tends to depend on the molecular environment of the label, including substances that are bound to the label covalently. Thus, it is generally important to minimize differences in the sample matrix (composition of background substances in the sample) when nonradioactive labels are being employed. This is not always controlled adequately, potentially leading to a loss in accuracy and precision of the analysis. However, it can be useful in certain analytical procedures that the signal from a label is sensitive to the molecular environment of the label, e.g., in fluorescence polarization ligand assays.

Another general limitation of currently available chemical labels is the loss in the assay sensitivity at some point when the sample of interest is progressively diluted to larger volumes prior to measurement of the signal associated with the label. This occurs because analytical procedures typically involve dilution steps arising from the addition of analytical reagents and solutions to the sample undergoing analysis, or from chromatographic separation steps, which generally, in the absence of enrichment mechanisms, cause dilution of the sample.

A particular shortcoming in the measurement of the class of labels called "electron absorbers", which are detected by their ability to absorb electrons in the vapor state, is that these labels have generally been employed only to measure molecules which are inherently volatile, or volatile after a labeling step. The most common technique for measuring molecules which contain electron-absorbing groups as labels is gas chromatography with electron capture detection (GC-ECD). In this technique, the sample to be analyzed is first injected into a gas chromatography column. The components in the sample are then separated in the volatile state by passage through the column. Finally, these components are detected based on their ability to capture gaseous electrons which comprise or influence an electrical current in an electron capture detector located at the exit of the column.

Label or signal groups frequently are combined with reactivity groups in order to allow covalent attachment of the label to the substance of interest. For example, a Bolton Hunter reagent is available commercially in which an $^{125}I$ radiolabel is incorporated into a reactive molecule of p-hydroxyphenyl-propionic acid active ester. This reactive labeling reagent is used especially to radiolabel peptides and proteins with $^{125}I$.

The use of reactive, electron-absorbing labeling reagents in chemical analysis has been reviewed recently (*Analytical Chemistry* 52, 1002A (1980)). These reagents are used to derivatize analytes to increase the sensitivity and volatility of the analytes for analysis by GC-ECD.

Label or signal groups have not been combined, however, with both reactivity and chemical release groups. These latter groups are defined as molecular groups which are specifically released by certain chemical reaction conditions to separate the signal group from the substance to which the labeling reagent has been attached. Two common examples of specific chemical release groups are methionylamides, which are split by cyanogen bromide; and 1,2-diol (vic-glycol) groups, which are split by periodate. The applications of methionylamide cleavage comprise generation of peptide fragments for sequencing (*Methods in Enzymology*, 11, 238 (1967)); removal of acylmethionine protecting groups in peptide synthesis (*Biochemistry* 13, 5159 (1974), and *Biochemical Journal* 165, 479 (1977)); and polypeptide uncoupling in protein synthesis by recombinant DNA techniques (*Science*, 198, 1056 (1977)).

A radiolabeled or otherwise labeled Edman reagent has been used to sequence polypeptides (see *J. Biol. Chem*, 250, 3629 (1975)); a process involving a release step. However, such Edman reagents do not incorporate a release group. The opportunity for release arises as a consequence of the attachment of the Edman reagent to a peptide of peptide equivalent. Splitting takes place at a site on the peptide near the attached Edman group, rather than within the attached Edman group. This applies as well to an Edman reagent which incorporates an electron absorbing group (*Proc. Soc. Exp. Biol. Med.*, 155, 287 (1977)).

A class of reagents called "protecting groups" are widely employed in peptide synthesis. These reagents are reactive, a few of them possess groups which can be detected, and these reagents ultimately are removed from the peptide after it is synthesized. However, protecting groups differ from release tags both functionally and structurally. The purpose of protecting groups is to facilitate synthesis rather than analysis, and their removal from the peptide, after this peptide is synthesized, necessarily involves a breakage of the bond previously made to the peptide by the reactivity group. Usually chemical cleavage is performed, but an ezyme-labeled protecting group also has been used (*Proceedings National Academy of Sciences* 72, 2193 (1975)).

In one case a signal group (phenylazo residue) was incorporated into a protecting group for peptide synthesis, allowing one to monitor colorimetrically or visually the purification of the protecting group-peptide adduct (*Helv. Chim. Acta* 41, 491 (1958)), in German; summarized in English on pages 17-18 in "*The Peptides*", Vol. 3, E. Gross and J. Meienhofer, Academic Press, 1981. However, this monitoring is performed without release of the signal group. Thus, one of the useful chemical conditions presented for removing the protecting group acceptably causes degradation and loss of color of the signal group.

A binding assay employing an enzyme-cleavable substrate as a label involving a conjugate compound has been introduced with the conjugate comprising the four-part structure "(galactosyl)-(umbelliferone)-(linking group)-(binding component)" (see U.S. Pat. Nos. 4,226,798 and 4,279,992). Enzymatic cleavage at the (galactosyl)-(umbelliferone) bond increases the intensity of the signal from the dye indicator umbelliferone group. However, there is no release of the umbelliferone signal group from the binding component, which binding component is the substance of interest.

SUMMARY OF THE INVENTION

My invention relates to a new class of analytical reagents called release tags and to the use of release tags in chemical analysis. My molecular release tags are useful as chemical labels in analytical procedures.

My release tags comprise three molecular groups, "signal", "release", and "reactivity", such that the signal and reactivity groups are separated by the release group, as indicated here and have the general formula S—Re—Rx where S is the signal group, Re is the release group, and Rx is the reactivity group.

The reactivity group allows the release tag to be attached covalently to a substance of interest, such as a ligand in a liquid medium, an analog thereof, or a specific binding partner thereof. The signal group is for detection purposes, comprising a molecular group or atom which can be detected with high sensitivity and specificity. The release group provides a site for specific chemical release. Splitting at this site releases the signal group from attachment to the substance of interest.

The reaction and release of a release tag compound with a substance of interest $S_I$ is illustrated by:

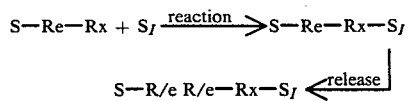

where the release group is split, typically and preferably by a chemical reaction although enzymatic cleavage may be used. The splitting of the release portion for the purpose of illustration only, is shown by a line between the R and e of the Re group; however, splitting may take place at any selected place at the release group, e.g., within the release group, so that after splitting, fragments of the release group are with the signal and the reactivity group, or such that the release group is entirely with the signal or reactivity group. Fragments of the release group may also be lost in the splitting process.

My release tags are intended prrmarily to enhance the usefulness of nonradioactive labels in chemical analysis. Any of the chemical labels or signal groups of the prior art as set forth in the Background of the Invention can be used as the signal group in my release tags. In all of these cases, the ability to release specifically the signal group from the substance to which it is attached can lead to an enhanced opportunity to extract, purify, and/or concentrate this signal group prior to its measurement. The signal group therefore potentially can be detected with more accuracy and precision than if it remains attached to the substance of interest, due to the removal of the signal group from interferences prior to measurement of this signal group. Also, the signal group potentially can be detected with more sensitivity because of the concentration step.

Another advantage arising from the use of my release tag reagents in chemical analysis is the enchanced opportunity to employ structural analogs of a given type of signal or release group, giving rise to a series of analogous release tags. In this case the released signal groups will be separated, e.g., by a chromatographic step, prior to detection. For example, separation-detection can be provided by GC-ECD in the case of volatile electron-absorbing signal groups. Or, as a second example, high performance liquid chromatography (hplc) with fluorescent detection can be used to separate and quantitate analogous, fluorescent signal groups after release of these signal groups from the substance of interest. The several, closely related forms of the released signal group thereby can be measured essentially simultaneously and with comparable sensitivity and complete discrimination. A single separation-detection process and set of conditions then can be used to measure a given set of homologous release tags (usually differing only in the structures of their signal or release groups) irrespective of the nature of the substances to which these release tags are attached. This advantage of a universal separation-detection step for the analysis of a wide variety of substances labeled with a given set of homologous release tags applies as well to measurements carried out even with a single release tag, as long as these labeled substances are separated prior to measurement.

In the particular case of a release tag in which the released signal group is inherently volatile, or can be made so by a suitable derivatization procedure, then the use of such a release tag affords the additional advantage that separation-detection techniques like GC-ECD are extended to the analysis of nonvolatile substances. A related, potential advantage is also realized when the released signal group can be extracted into an organic solvent. In this case, the released signal group potentially can be isolated from an aqueous sample by extraction with an immiscible, highly volatile organic solvent, and then readily concentrated by evaporation. Whenever the released signal group can be extracted in this or an analogous manner, but the release tag analyte conjugate is not extractable, then appropriate pre-extraction of the sample being analyzed, prior to chemical release of the signal group, can be used to remove extractable interferences before the signal group is released and extracted. Ion-pair extractions, solid phase extractions, gas phase extractions, etc., are all relevant procedures.

Finally, in the particular case of a release tag in which the released signal group is inherently volatile, and also is a highly electron-absorbing group, then the opportunity exists for ultrasensitive analysis with the use of such a release tag in conjunction with separation-detection by GC-ECD. For example, we have observed a detection limit of 90 attograms ($1.6 \times 10^{-19}$ mole) when the highly electron-absorbing compound, N-N-dipentafluorbenzoyl-pentafluoroaniline is analyzed by GC-ECD.

As an illustrative example of the relese tags of my invention, I have synthesized N-pentafluorobenzoyl-methionyl-glycine-N-hydroxysuccinimide ester (N-PFB-Met-Gly-NHS) the structural formula of which is

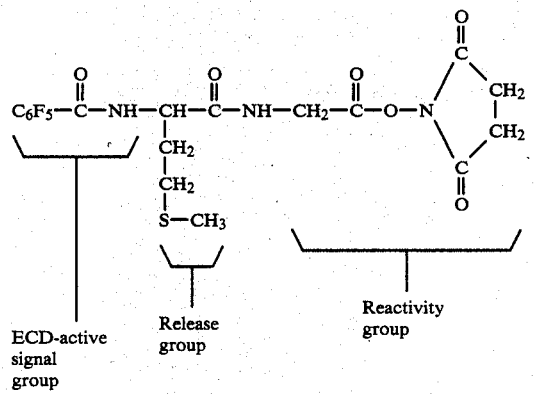

In this release tag, the signal group is N-PFB (sensitive by GC-ECD), the release group is methionylamide (susceptible to specific chemical release by cyanogen bromide, releasing the signal group as a nonpolar and volatile N-PFB-homoserine lactone), and the reactivity group is NHS (reacts especially with primary amino groups). The structural formula of the released signal group is

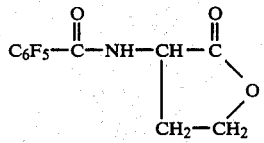

In an illustrative example of the use of this release tag, the release tag is used to analyze the hormone, thyroxine ($T_4$), in serum. The $T_4$ is first extracted from serum at high pH, and then this $T_4$ is purified by ion exchange chromatography. The $T_4$ analogue, 3',5'-dibromo-3,5-diiodothyronine ($Br_2T_2$) is added as an internal standard. The $T_4$ and $Br_2T_2$ are reacted covalently with the reactivity group of the release tag, N-PFB-Met-Gly-NHS, and the resulting tag-$T_4$ and tag-$Br_2T_2$ products are separated by high performance liquid chromatography and collected. The signal group is released from these two products by means of reaction with cyanogen bromide, and then quantitated by GC-ECD. The resulting quantitative value for $T_4$ agrees with that obtained by radioimmunoassay. Corresponding analysis of a hypothyroid serum, and of a serum blank containing no $T_4$, give results establishing control of interferences.

Other choices of signal groups/signal analysis methods besides N-PFB/GC-ECD include, but are not limited to: N-heptafluorobutyrl or N-p-(pentafluorophenoxy)-2,3,5,6-tetrafluorobenzoyl or pentachlorophenyl/GC-ECD or negative chemical ionization mass spectrometry; fluorescein or rhodamine or dansyl or umbelliferyl or o-phthalyl/± liquid chromatography (LC) with fluorescence (or laser fluorescence) detection; N-3,5-dinitrobenzoyl or 4-N,N-dimethylazobenzene/± LC with absorbance detection; luminol or isoluminol/± LC with luminescence detection; ferrocene or cobalticinium/± LC with atomic absorption detection; nitroxide/± LC with electron spin resonance detection; $^3$H-acetyl or $^{35}$S-phenylthiocarbamate or $^{125}$I-Bolton Hunter Reagent/± LC with radioactivity detection; N-nitrosodiphenylamine or alkylnitrite or arylnitrite/± LC or± GC with thermal energy analysis or pyrolysis-resonance ionization spectroscopy detection; and nicotinamide adenine dinucleotide coenzyme/± LC with dehydrogenase enzyme reaction and fluorescence or absorbance or visual detection.

Other choices of specific chemical release groups/specific chemical reaction release conditions include, but are not limited to, 1,2-diol/periodate; disulfide/mercaptoethanol; tryptophan or tyrosine/o-iodosobenzoic acid; thioester/hydroxylamine; azo group/sodium hydrosulfite; α-toluenesulfonic ester of a α,γ-acetylenic alcohol/sodium iodide; olefin/ozone; benzyl ether/catalytic hydrogenation; alkyl, phenyl ether/hydrobromic acid; hydrazone/acetylacetone; thioether/cyanogen bromide; benzylether/hydrogenolysis; benzyloxycarbonylamine/hydrogenation; alkyl- or arylsulfonylethyloxycarbonylamine/alkali; alkyl or arylthioethyl-oxycarbonylamine/oxidation-alkali; tosylamine/electrolytic reduction; S-benzylether/electrolytic reduction; O-nitrobenzylamide/photolysis; 2-nitro-4,5-dimethoxy-benzyloxycarbonylamine/photolysis; amine oxide/pyrolysis(Cope elimination reaction); xanthate/pyrolysis (Chugaev reaction); and quaternary ammonium hydroxide/pyrolysis (Hofmann elimination reaction).

Other choices of reactivity groups include, but are not limited to, p-nitrophenyl ester, silyl halide, sulfonyl halide, acid halide, acid anhydride, α-halo-ketone, dione, maleimide, diazonium, imidoester, aldehyde, halonitrophenyl, arylazide, isothiocyanate, epoxide, carbene, nitrene, sulfenyl halide, amino and hydrazide. Further choices of signal group/signal analysis methods, reactivity groups and release groups would be apparent to those skilled in the art.

These reactivity groups collectively provide a wide variety of specific as well as general reactivities, allowing release tags to be attached covalently to many kinds of substances to be quantitated, where such substances will each contain or can be provided with one or more functional groups capable of being reacted with the reactivity group on the release tag. Examples of such functional groups on substances to be quantitated, or functional groups which can be provided on this substance, are amino, carboxyl, hydroxy, guanidino, imidazole, thiol, phenol and aldehyde.

Examples of release tag compounds other than N-PFB-Met-Gly-NHS are: (1) N-PFB-α-methyl-Met-Gly-NHS (which differs from the initial release only by substitution of a $CH_3$ in place of an H group in the release group part of the molecule, and thereby is useful for preparing an internal standard to be employed along with the use of N-PFB-Met-Gly-NHS); (2) N-Dansyl-Met-Gly-p-nitrophenyl ester (which illustrates the use of alternate signal and reactivity groups with the same release group as used initially, where the dansyl group is a fluorescent signal group); (3) N-3,5-Dinitrobenzoyl-Met-Gly-imido ester (which further illustrates alternative signal and reactivity groups with the same release group as used initially, where the dinitrobenzoyl group is an absorbance signal group); (4) N-PFB-Met(0)-Gly-NHS (which incorporates a methionine sulfoxide in place of a methionine group, which release tag comprises a tag in which the release group is more inert and protected from CNBr cleavage until the Met(0) group is chemically reduced to a Met group; (5) N-PFB-6-amino-4-methyl-3,4-dihydroxyhexanoic acid NHS ester (which illustrates the use of an alternate release group, i.e., a vicdiol release group, in combination with the same signal and reactivity groups as used initially); (6) p-Ferrocenyl-phenethyl (p-isothiocyanatobenzyl)-(methyl) amine oxide (which illustrates a release tag with completely different signal, release and reactivity groups than used initially, where the ferrocenyl signal group is measured by atomic absorption, the phenethyl-amine oxide release group is released thermally by a Cope elimination reaction, and the isothiocyanatobenzyl group constitutes a reactivity group); and, (7) p-(4-Pentachlorophenoxy-benzyloxy)-phenylsulfonylchloride (which also illustrates a release tag with completely different signal, release and reactivity groups than used initially, where the pentachlorophenoxy group is electron absorbing, the benzyloxy release group is released by hydrogenolysis, and the phenylsulfonyl chloride part is a reactivity group. A large number of release tag compounds can be defined based on the previous list of signal, release and reactivity groups, and from analogous signal, release and reactivity groups.

Examples of types of substances of interest which can be analyzed with the use of release tags are hormones, receptors, drugs, vitamins, prostaglandins, ecdysones, neurotransmitters, metabolites, enzymes, toxins, genes, DNA-carcinogen adducts, chemical and biological warfare agents, poisons, pesticides, viruses, bacteria and smoke particles. Further examples of substances which can be analyzed with the use of release tags would be familiar to one skilled in the art.

EXAMPLE

Synthesis of N-pentafluorobenzoyl-methionyl-glycine-N-hydroxysuccinimide ester (N-PFB-Met-Gly-NHS).

480 mg (2.3 mmole) of methionylglycine were dissolved in 4 ml water, the pH was adjusted to 9 with 3 M sodium hydroxide, and the solution was cooled in ice. 0.4 ml (2.7 mmole) of pentafluorobenzoyl chloride was added in small portions over a period of 2 hours, while the pH was kept around 9. The reaction mixture was diluted with 40 ml water and acidified with 10% hydrochloric acid. After ethyl acetate extraction and drying under vacuum, the product was recrystallized from ethyl acetate/heptane; 84% yield; mp 154°–156° C.; and was a single peak on hplc except for a small peak (ca. 5%) of pentafluorobenzoic acid. The structure was confirmed by reacting the product with 25% (by weight) dry ethanolic HCl for 5 min at room temperature, and observing the expected molecular ion (m/e 428) by mass spectrometry for the corresponding ethyl ester, a single peak on hplc. To 160 mg (0.4 mmole) of N-PFB-Met-Gly (dried over $P_2O_5$ under high vacuum) dissolved in 5 ml of dry dioxane and 5 ml of methylene chloride, 92 mg (0.45 mmole) of distilled N,N-dicyclohexylcarbodiimide dissolved in 1 ml of methylene chloride were added and the solution was cooled to ice temperature. After the addition of 45 mg (0.4 mmole) of dry N-hydroxysuccinimide dissolved in 1 ml of dioxane, the reaction mixture was allowed to warm up to room temperature. After 5 hours the precipitated N,N-dicyclohexylurea was filtered, the filtrate was evaporated, and the residue was dissolved in methylene chloride. Precipitated urea was filtered again. N-PFB-Met-Gly-N-hydroxyccinimide ester was crystallized from methylene chloride/heptane, m.p. yield 47%.

Preparation of a solution of N-(N-PFB-Met-Gly)-$T_4$ (tag-$T_4$) and N- (N-PFB-Met-Gly)-$Br_2T_2$ (tag-$Br_2T_2$).

0.19 ug (0.24 nmole) of $T_4$ and 0.18 ug (0.26 nmole) of $Br_2T_2$ were dissolved in 100 ul of tetrahydrofuran. To this solution was added 68 ug (0.14 umole) of N-PFB-Met-Gly-NHS ester dissolved in 100 ul of tetrahydrofuran, and 1 ul of N-methyl-morpholine. The reaction mixture was kept at room temperature for 2 hours. The solvent was evaporated and the residue was dissolved in 100 ul of hplc mobile phase and analyzed by hplc. Single peaks for tag-$T_4$ and tag-$Br_2T_2$ were observed at 14 and 11.4 min, respectively. (These retention times had been established in prior work with pure samples or tag-$T_4$ and $Br_2T_2$). No starting material was present.

Sample Cleanup.

To 0.8 ml of serum, 8 ul of 1 M sodium hydroxide was added. After 5 min standing, the serum was treated with 1.3 ml of acetonitrile and the resulting precipitate was spun down. The supernate was applied to a small anion exchange column (Bio-Rad AG 1-X2, 200-400 mesh, 5 cm×5 mm) which had been prewashed three times with 1 ml of 0.01 M NaOH (containing 25% isopropanol). After the sample application, the column was washed with the following solvents, all containing 25% isopropanol; 2×1 ml 0.01 MNaOH; 3×1 ml 0.2 M ammonium acetate pH 9.0; 1×1 ml 0.2 M ammonium acetate pH 6.9, 2×1 ml 0.2 M ammonium acetate pH 4.6, and 3×1 ml of 15% acetic acid solution. Then thyroxine ($T_4$) was eluted with 2×1 ml acetic acid/methanol/water (6:2:2). The collected sample was evaporated to dryness, under high vacuum.

Derivatization of $T_4$ 90 ng of $Br_2T_2$ was added as an internal standard, together with 100 ul of ethanol and 10 ul of N-methyl-morpholine. The sample was evaporated again under high vacuum to remove residual acid and water. For the derivatization, 0.11 mg of N-PFB-Met-Gly-NHS in 100 ul of tetrahydrofuran was added together with 1 ul of N-methyl-morpholine. After two hours reaction time at room temperature, the sample was evaporated to dryness under high vacuum.

Separation of tag-T₄ and tag-Br₂T² by high performance liquid chromatography (hplc)

The sample was dissolved in 100 ul of the hplc solvent mixture (10 mM $KH_2PO_4$, pH 2.1/acetonitrile; 53%/47%), and 25 ul of the resulting solution were injected onto a C18, 15 cm×4.6 mm Supelcosil hplc column. The sample was eluted with the same solvent mixture at a flow rate of 2 ml/min. The fractions containing tag-$Br_2T_2$ and tag-$T_4$ were collected separately and evaporated under high vacuum.

Release and quantitation of the N-PFB homoserine lactone (N-PFB-Hse lactone) signal group 200 ul of formic acid (70%) and 10 ul of a 1 M solution of cyanogen bromide in ethanol were added to each of the collected samples. The closed vials were heated for one hour at 70° C., and then the samples were evaporated under nitrogen, and the residues were dissolved in 50 ul of toluene. 1 ul of each solution then was injected into a gas chromatograph fitted with an electron capture detector (GC-ECD). The peak for the released signal group, N-PFB-Hse lactone, was quantitated by comparison with an injection of a known amount of a pure sample of this substance. The amounts of $T_4$ and $Br_2T_2$ were calculated based on the amount of lactone detected in the corresponding samples from tag-$T_4$ and tag-$Br_2T_2$. The value for $T_4$ was 6.7 ug/dl, in good agreement with values of 7.1 and 7.6 ug/dl for $T_4$ obtained independently by radioimmunoassay for this serum sample.

What I claim is:

1. A molecular conjugate, comprising: a release tag compound covalently bound to an analyte to be analytically determined or to a specific binding partner thereof; said specific binding partner being selected from the group consisting of antibodies for the analyte, and DNA probes; said release tag compound comprising:

a signal group S, a release group Re, and a reactivity group Rx, group S being covalently linked to group Re, and group being further covalently linked to group Rx to define structure S—Re—Rx for said compound;

Rx further comprising a functional group capable of forming a covalent bond with another molecule, said functional group being selected from the group consisting of silyl halides, sulfonyl halides, acid halides, acid anhydrides, α-halo ketones, diones, maleimides, diazonium salts, imidoesters, aldehydes, halogenated nitrophenyls, arylazides, isothiocyanates, epoxides, carbenes, nitrenes, sulfenyl halides, amines, and hydrazides;

Re further comprising a functionality selected from the group consisting of methionylamides, vicinyl glycols, olefins, β-phenylethylamine oxides, and benzyl ethers; and S further comprising a halogenated electron-absorbing organic group;

groups S and Re being mutually selected such that upon cleavage of said release tag at release group Re, signal group S is released in a volatile form suitable for electron capture determination in the gas phase.

2. The molecular conjugate of claim 1 wherein the signal group S is selected from th group consisting of pentafluorobenzoyl, heptafluorobutyryl, p-(pentafluorophenoxy)-2,3,5,6,-tetrafluorobenzoyl, and pentachlorophenyl.

3. The molecular conjugate of claim 34 wherein the release group Re is selected from the group consisting of methionyl-glycyl, α-methyl methionyl-glycyl, methionylsulfoxide-glycyl, and 6-amino-4-methyl- 3,4-dihydroxyhexanoyl functionalities.

4. The molecular conjugate of claim 1 wherein the reactivity group Rx is selected from the group consisting of N-hydroxysuccinimide ester, p-nitrophenyl ester, phenylisothiocyanate, and phenylsulfonyl chloride.

5. A release tag compound, selected from the group consisting of:
(a) N-pentafluorobenzoyl-α-methyl-methionyl-glycine-N-hydroxysuccinimide ester;
(b) N-pentafluorobenzoyl-methionyl sulfoxide-glycine-N-hydroxysuccinimide ester;
(c) N-pentafluorobenzoyl-6-amino-4-methyl-3,4 dihydroxy hexanoic acid-N -hydroxysuccinimide ester;
(d) p-(4-pentachlorophenoxy-benzyloxy)-phenylsulfonyl chloride.

6. A release tag compound, comprising:
N-pentafluorobenzoyl-methionyl-glycine-N-hydroxysuccinimide ester, having the formula

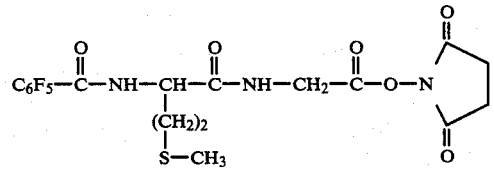

7. A molecular conjugate, comprising: a release tag compound covalently bound to an analyte to be analytically determined or to a specific binding partner thereof; said specific binding partner being selected from the group consisting of antibodies for the analyte, and DNA probes; said release tag compound comprising:

a signal group S, a release group Re, and a reactivity group Rx, group S being covalently linked to group Re, and group Re being further covalently linked to group Rx to define structure S—Re—Rx for said compound;

Rx further comprising a functional group capable of forming a covalent bond with another molecule; said functional groups being selected from the group consisting of silyl halides, sulfonyl halides, acid halides, acid anhydrides, α-halo ketones, diones, maleimides, diazonium salts, imidoesters, aldehydes, halogenated nitrophenyls, arylazides, isothiocyanates, epoxides, carbenes, nitrenes, sulfenyl halides, amines, and hydrazides;

Re further comprising a functionality selected from the group consisting of disulfides, tryptophan, tyrosine, thioesters, azo compounds, p-toluensulfonic esters of β, γ-acetylenic alcohols, alkyl phenyl ethers, hydrazones, thioethers, benzoyloxycarbonylamines, alkylsulfonylethoxycarbonylamines, arylsufonylethoxycarbonylamines, alkylthioethyloxycarbonylamines, arylthioethyloxycarbonylamines, tosylamines, S-benzylethers, o-nitrobenzylamides, 2-nitro- 4,5-dimethoxy-benzyloxycarbonylamnes, amine oxides, and xanthates; and S further comprising a halogenated electron-absorbing organic group;

group S and Re being mutually selected such that upon cleavage of said release tag at release group Re, signal group S is releases in a volatile form suitable for electron capture determination in the gas phase.

8. The molecular conjugate of claim 7 wherein the signal group S is selected from the group consisting of pentafluorobenzoyl, heptafluorobutyryl, p-(pentafluorophenoxy)-2,3,5,6-tetrafluorobenzoyl, and pentachlorophenyl.

9. The molecular conjugate of claim 7 wherein the release group Re is selected from the group consisting of methionyl-glycyl, α-methyl methionyl-glycyl, methionylsulfoxide-glycyl, and 6-amino-4-methyl-3,4-dihydroxyhexanoyl functionalities.

10. The molecular conjugate of claim 7 wherein the reactivity group Rx is selected from the group consisting of N-hydroxysuccinimide ester, p-nitrophenyl ester, phenylisothiocyanate, and phenylsulfonyl chloride.

* * * * *

UNITED STATES PATENT AND TRADEMARK OFFICE
CERTIFICATE OF CORRECTION

PATENT NO. : 4,709,016  (Page 1 of 2)
DATED : November 24, 1987
INVENTOR(S) : Roger W. Giese It is certified that error appears in the above-identified patent and that said Letters Patent is hereby corrected as shown below:

| | | |
|---|---|---|
| Column 1, | line 32, | "specifc" should read --specific-- |
| Column 3, | line 1, | "peptide of peptide" should read --peptide or peptide-- |
| | line 19, | "labeled" should read --labile-- |
| Column 4, | line 22, | "prrmarily" should read --primarily-- |
| Column 5, | line 26, | "fluorbenzoyl-pentafluoroaniline" should read --fluorobenzoyl-pentafluoroaniline-- |
| Column 6, | line 42, | "α-toluenesulfonic ester of a α,γ-acetylenic" should read --p-toluenesulfonic ester of a β,γ-acetylenic-- |
| Column 7, | line 31, | "vicdiol" should read --vic-diol-- |
| Column 8, | line 42, | "samples or" should read --samples of-- |
| | line 55, | "MNaOH;" should read --M NaOH;-- |
| Column 9, | line 6, | "tag-$Br_2T^2$" should read --tag-$Br_2T_2$-- |
| | line 46, | "group being" should read --group Re being-- |
| Column 10, | line 2, | "from th group" should read --from the group-- |

UNITED STATES PATENT AND TRADEMARK OFFICE
CERTIFICATE OF CORRECTION

PATENT NO. : 4,709,016

DATED : November 24, 1987

INVENTOR(S) : Roger W. Giese

It is certified that error appears in the above-identified patent and that said Letters Patent is hereby corrected as shown below:

Column 10, line 6,    "claim 34" should read --claim 1--

Column 11, line 1,    "zyloxycarbonylamnes," should read --zyloxycarbonylamines--

Column 11, line 7,    "is releases" should read --is released--

Signed and Sealed this

Twenty-fifth Day of April, 1989

Attest:

DONALD J. QUIGG

Attesting Officer     Commissioner of Patents and Trademarks